US007009086B2

(12) United States Patent
Brown et al.

(10) Patent No.: US 7,009,086 B2
(45) Date of Patent: Mar. 7, 2006

(54) USE OF MOLECULAR SIEVES FOR THE CONVERSION OF OXYGENATES TO OLEFINS

(75) Inventors: Stephen H. Brown, Brussels (BE); Richard B. Hall, Whitehouse Station, NJ (US); Karl G. Strohmaier, Port Murray, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 309 days.

(21) Appl. No.: 10/283,117

(22) Filed: Oct. 29, 2002

(65) Prior Publication Data

US 2004/0082825 A1  Apr. 29, 2004

(51) Int. Cl.
*C07C 1/00*  (2006.01)

(52) U.S. Cl. ..................................... 585/640; 585/639

(58) Field of Classification Search .............. 585/639, 585/640

See application file for complete search history.

(56) References Cited

U.S. PATENT DOCUMENTS

| 4,449,327 A | 5/1984 | Nielsen ..................... 49/390 |
| 5,126,308 A | 6/1992 | Barger et al. ............... 502/214 |
| 5,191,141 A | 3/1993 | Barger et al. ............... 585/640 |
| 5,912,393 A | 6/1999 | Barger et al. ............... 585/641 |
| 6,207,872 B1 | 3/2001 | Barger et al. ............... 585/640 |
| 6,534,692 B1 | 3/2003 | Barger et al. ............... 585/640 |

FOREIGN PATENT DOCUMENTS

| EP | 1 214 974 | 6/1902 |
| EP | 0 993 867 | 4/2000 |
| WO | WO 98/15496 | 4/1998 |
| WO | WO 00/06493 | 2/2000 |
| WO | WO 01/23500 | 4/2001 |
| WO | WO 01/36328 | 5/2001 |
| WO | WO 02/076612 | 3/2002 |
| WO | WO 02/070407 | 9/2002 |

OTHER PUBLICATIONS

Atlas of Zeolite Framework Types, 5th Edition, pp. 96-97 (2001).

Wilson et al., "Microporous and Mesoporous Materials", vol. 29, pp. 117-126 (1999).

Dahl et al., *"The effect of Cyrstallite Size on the Activity and Selectivity of the Reaction of Ethanol and 2-propanol over SAPO-34,"* Microporous and Mesoporous Materials, vol. 29, pp. 159-171, (1999).

Primary Examiner—Elizabeth D. Wood

(57) ABSTRACT

This invention relates to a process for converting an oxygenate feedstock to light olefins using a crystalline metalloaluminophosphate molecular sieve having a high metal content and a small particle size. It also relates to crystalline metalloaluminophosphate molecular sieves with high metal content and a small particle size.

13 Claims, 1 Drawing Sheet

USE OF MOLECULAR SIEVES FOR THE CONVERSION OF OXYGENATES TO OLEFINS

This invention claims priority to applications U.S. Ser. No. 09/997,778 and U.S. Ser. No. 09/997,779 both filed on Nov. 29, 2001, the entire disclosures of which are incorporated herein by reference.

FIELD OF THE INVENTION

This invention relates to a process for converting an oxygenate feedstock to light olefins using a crystalline metalloaluminophosphate molecular sieve having a high metal content and a small particle size. It also relates to crystalline metalloaluminophosphate molecular sieves with high metal content and a small particle size.

BACKGROUND OF THE INVENTION

Olefins, particularly light olefins, have been traditionally produced from petroleum feedstocks by either catalytic or steam cracking. Oxygenates, however, are becoming an alternative feedstock for making light olefins, particularly ethylene and propylene. Promising oxygenate feedstocks are alcohols, such as methanol and ethanol, dimethyl ether, methyl ethyl ether, diethyl ether, dimethyl carbonate, and methyl formate. Many of these oxygenates can be produced from a variety of sources including natural gas. Because of the relatively low-cost of these sources, alcohol, alcohol derivatives, and other oxygenates have promise as an economical source for light olefin production.

One way of producing olefins is by the conversion of methanol to olefins (MTO) catalyzed by a molecular sieve. Some of the most useful molecular sieves for converting methanol to olefin(s) are the metalloaluminophosphates such as the silicoaluminophosphates (SAPO's). For example, U.S. Pat. No. 4,499,327 to Kaiser, fully incorporated herein by reference, discloses making olefins from methanol using a variety of SAPO molecular sieve catalysts. The process can be carried out at a temperature between 300° C. and 500° C., a pressure between 0.1 atmosphere to 100 atmospheres, and a weight hourly space velocity (WHSV) of between 0.1 and 40 hr$^{-1}$.

SAPO molecular sieves contain a three-dimensional microporous crystal framework structure of [SiO$_2$], [AlO$_2$] and [PO$_2$] corner sharing tetrahedral units. The number of [SiO$_2$] tetrahedral units is related to the acidic properties of the SAPO molecular sieve: the higher the Si content, the higher the molecular sieve acidity.

There are a wide variety of SAPO molecular sieves known in the art. Of these the more important examples as catalysts for the conversion of oxygenates to olefins include SAPO-5, SAPO-11, SAPO-18, SAPO-34, SAPO-35, SAPO-41, and SAPO-56. SAPO molecular sieves having the CHA framework type and especially SAPO-34 are particularly important catalysts. The CHA framework type has a double six-ring structure in an ABC stacking arrangement. The pore openings of the structure are defined by eight member rings that have a diameter of about 4.0 Å, and cylindrical cages within the structure of approximately 10×6.7 Å type ("Atlas of Zeolite Framework Types", 2001, 5th Edition, p. 96–97). SAPO-34 crystals have a cubic-like morphology and typically crystallize as cubes, partial cubes, platelets or flakes, depending on the height of the crystals. Other SAPO molecular sieves of CHA framework type include SAPO-44, SAPO-47 and ZYT-6.

Another important class of SAPO molecular sieves consists of mixed or intergrown phases of molecular sieves having the CHA and AEI framework types. Examples of such materials are disclosed in WO98/15496, published 16 Apr. 1998, and in PCT WO02/070407, published Sep. 12, 2002, both herein fully incorporated by reference.

U.S. Pat. Nos. 5,126,308 and 5,191,141 to Barger et al., herein fully incorporated by reference, disclose a method for converting methanol to light olefins using an ELAPO catalyst. The catalyst comprises a metal aluminophosphate molecular sieve having the empirical formula (EL$_x$Al$_y$P$_z$)O$_2$ where EL is a metal and x, y and z are mole fractions of EL, Al and P respectively. Preferred EL metals are silicon, magnesium and cobalt, with silicon especially preferred. According to these documents, small particle size SAPO-34 having low Si/Al ratios have a longer life and increased selectivity over other types of SAPOs when used as catalysts in MTO processes. These documents also describe a process for the manufacture of SAPO-34 of median particle diameters, expressed as a mass distribution, in the range of about 0.6 to 1.4 μm, in which the molecular sieve synthesis mixture is stirred. As the amount of metal is lowered, the particle size is also reduced.

Wilson, et al. reported that it is beneficial to use SAPO molecular sieves having low Si content for MTO conversions (*Microporous and Mesoporous Materials*, 29, 117–126, 1999, incorporated herein by reference). According to Wilson, SAPOs with low Si content deactivate slower and produce less undesired products than other SAPOs when used in MTO conversions.

PCT WO 01/23500 published Apr. 5, 2001 discloses a method for making an olefin product from an oxygenate-containing feedstock. In the method, a silicoaluminophosphate molecular sieve catalyst is contacted with the oxygenate-containing feedstock in a reactor at an average catalyst feedstock exposure (ACFE) index of at least 1.0. For a given catalyst used under such conditions, the method produces lower coke yield and provides an olefin product which is lower in C1–C4 paraffin content than when the ACFE index is lower than 1.0. According to example 1 and FIG. 1 of this document, SAPOs with low Si/Al atomic ratios are preferred in order to mimimize selectivity to propane.

We have now found that crystalline metalloaluminophosphate molecular sieves, preferably crystalline silicoaluminophosphate (SAPO) molecular sieves, having a small particle size and a high metal, preferably Si, content have excellent catalytic performances when used in MTO processes.

SUMMARY OF THE INVENTION

The present invention accordingly provides a process for converting an oxygenate feedstock to light olefins which comprises contacting the oxygenate feedstock under catalytic conversion conditions with a catalyst, the catalyst comprising a crystalline metalloaluminophosphate molecular sieve having a chemical composition on an anhydrous basis expressed by an empirical formula of $$(EL_xAl_yP_z)O_2$$

where EL is a metal selected from the group consisting of silicon, germanium and mixtures thereof, "x" is the mole fraction of EL and has a value of greater than 0.05, "y" is the mole fraction of Al and has a value of at least 0.01, "z" is the mole fraction of P and has a value of at least 0.01 and x+y+z=1, the molecular sieve crystals having at least one crystal dimension of less than 0.20 micron, preferably of less than 0.15 micron, more preferably of less than 0.10 micron. In an embodiment, the molecular sieve crystals have all crystal dimensions of less than 0.20 micron.

In an embodiment of the molecular sieve used in the process of the present invention, x has a value preferably of at least 0.07, more preferably of at least 0.08, even more preferably of at least 0.085 and most preferably of at least 0.09.

In another embodiment, x/y is greater than 0.15, preferably, x/y is at least 0.17 and most preferably, x/y is at least 0.18.

In yet another preferred embodiment, El is silicon.

In a further embodiment, the molecular sieve is preferably selected from the group consisting of SAPO-5, SAPO-11, SAPO-18, SAPO-34, SAPO-35, SAPO-41, SAPO-56, mixtures thereof and intergrown forms thereof. Most preferably, the molecular sieve is SAPO-34.

For the process of the invention, the oxygenate is preferably selected from methanol, dimethyl ether and mixtures thereof. Most preferably, the oxygenate is methanol.

The present invention also relates to the molecular sieves suitable for use in the process of the present invention. Accordingly, an embodiment of the present invention is directed to a crystalline silicoaluminophosphate molecular sieve having a chemical composition on an anhydrous basis expressed by an empirical formula of $(Si_xAl_yP_z)O_2$ 

where "x" is the mole fraction of Si and has a value of greater than 0.05, "y" is the mole fraction of Al and has a value of at least 0.01, "z" is the mole fraction of P and has a value of at least 0.01 and x+y+z=1, the molecular sieve crystals having at least one crystal dimension of less than 0.20 micron, preferably of less than 0.15 micron, more preferably of less than 0.10 micron.

In yet another embodiment, the present invention relates to a crystalline silicoaluminophosphate molecular sieve having a chemical composition expressed by an empirical formula of $nR(Si_xAl_yP_z)O_2$ 

where R is a template, "n" is the mole fraction of template and has a value of at least 0.01, "x" is the mole fraction of Si and has a value of greater than 0.05, "y" is the mole fraction of Al and has a value of at least 0.01, "z" is the mole fraction of P and has a value of at least 0.01 and x+y+z=1, the molecular sieve crystals having at least one crystal dimension of less than 0.2 micron.

DETAILED DESCRIPTION OF THE INVENTION

Figure 1:
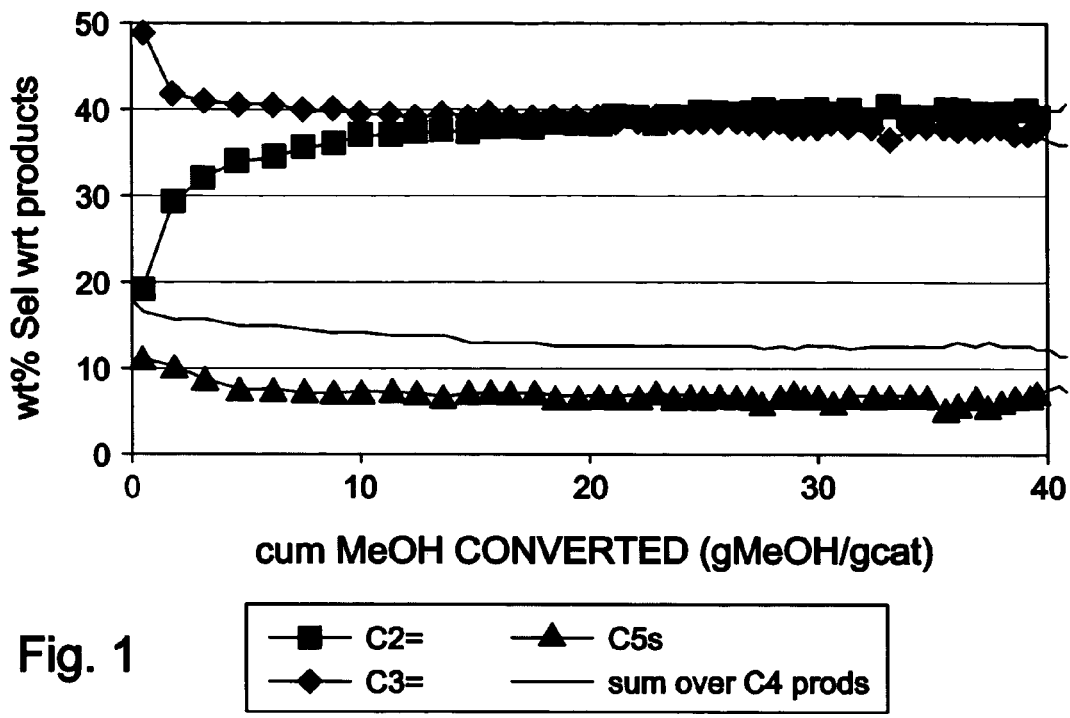
FIG. 1 shows the selectivities for ethylene (C2=), propylene (C3=), hydrocarbon products having 4 carbon atoms and hydrocarbon products having 5 carbon atoms for a SAPO-34 having crystal dimensions of from 0.5 to 1.0 micron and a Si/Al atomic ratio of 0.175.

The present invention is based on the observation that crystalline metalloaluminophosphate molecular sieves, preferably crystalline silicoaluminophosphate (SAPO) molecular sieves, that have a small particle size and a high metal, preferably Si, content have excellent catalytic performances when used in MTO processes. The belief prior to this invention was that, when used in MTO processes, metalloaluminophosphate (ELAPO) molecular sieves with small particle size and low metal content provided fewer by-products and deactivated less quickly than other ELAPOs. Such properties provide significant advantages in commercial scale operations: the processes are simpler and cheaper because fewer by-products are formed and the catalyst needs to be regenerated less often due to its long catalyst life.

We have surprisingly found that metalloaluminophosphate (ELAPO) molecular sieves, preferably SAPOs, with small particle size and high metal, preferably Si, content perform at least as well as SAPOs with low Si content and small particle size. In addition, the ELAPOs of the present invention have a high metal content. This means that the same degree of catalytic activity, i.e. the same number of acid or catalytic sites, can be obtained with less molecular sieve than when the metal content in the molecular sieve is low.

The molecular sieves of the present invention are crystalline metalloaluminophosphate molecular sieve having a chemical composition on an anhydrous basis expressed by an empirical formula of $(EL_xAl_yP_z)O_2$ 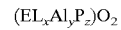

where EL is a metal selected from the group consisting of silicon, germanium and mixtures thereof, "x" is the mole fraction of EL and has a value of greater than 0.05, preferably at least 0.07, "y" is the mole fraction of Al and has a value of at least 0.01, "z" is the mole fraction of P and has a value of at least 0.01 and x+y+z=1, the molecular sieve crystals having at least one crystal dimension of less than 0.20 micron, preferably of less than 0.15 micron, more preferably of less than 0.10 micron. Preferably, EL is silicon.

The metalloaluminophosphate molecular sieves of the invention can have a variety of crystal morphologies, depending on the crystal framework type and symmetry. The preferred metalloaluminophosphate molecular sieves have the CHA framework type, and most preferably are SAPO-34. In another embodiment, the preferred crystal morphology is cubic or cubic-like. Cubic-like as used herein means that the crystals are not cubes in the strictest sense (rhombohedral with alpha, beta and gamma angles of exactly 90°), but are almost cubic (rhombohedral with alpha, beta and gamma angles close to, but not exactly equal to, 90°). Molecular sieves with cubic or cubic-like morphology can be in the form of cubes, partial cubes (cubes with a height less than the other two crystal edges), platelets or even flakes, depending on the crystal height. Preferably, the crystals are cubes or partial cubes.

The molecular sieve crystals of the present invention have at least one crystal dimension of less than 0.20 micron, preferably less than 0.15 micron, more preferably less than 0.1 micron. In the embodiment in which the crystals have cubic or cubic-like morphology, this means that at least one edge of all crystals is smaller than 0.2 micron, preferably smaller than 0.15 micron, more preferably smaller than 0.10 micron, as determined by electron microscopy. In a separate embodiment, the crystals have at least one dimension of less than 0.20 micron, and have at least one other dimension smaller than 0.2 micron, preferably smaller than 0.15 micron, more preferably smaller than 0.10 micron. In yet another separate embodiment, all crystal dimensions are smaller than 0.2 micron, preferably smaller than 0.15 micron, more preferably smaller than 0.10 micron.

In an embodiment of the invention, the x/y atomic ratio of the molecular sieve is greater than 0.15, preferably from 0.17 to 0.25. The x/y atomic ratio is conveniently determined by elemental analysis of the molecular sieve, on an anhydrous basis.

The molecular sieves of the present invention are obtained by hydrothermal treatment of a synthesis mixture comprising at least one source of EL metal, at least one source of aluminum and at least one source of phosphorus.

As source for the phosphorus in the synthesis mixture, there may be mentioned phosphoric acid, organic phosphates, e.g., triethylphosphate, and aluminophosphates.

As source for the aluminum in the synthesis mixture there may be mentioned alumina hydrate, alumina, sodium aluminate, pseudoboehmite, aluminum phosphate, organic aluminum sources, e.g., alkoxides, for example, aluminum isopropoxide.

In the case where EL is silicon, silicon sources include fumed silica, e.g., that sold under the trade name Aerosil; aqueous colloidal suspensions of silica, e.g., that sold under the trade name Ludox AS40, Ludox HS40 or Hydroseal HS40; or organic silicon sources. In a preferred embodiment, the silicon source is an organic silicon source, e.g., a tetraalkyl orthosilicate, for example, tetramethyl orthosilicate, tetraethyl orthosilicate, tetrapropyl orthosilicate, and tetrabutyl orthosilicate, more preferably tetraethyl orthosilicate (TEOS).

In addition, the synthesis mixture will usually contain an organic structure-directing agent (template). Templates include especially amines and quaternary ammonium compounds, used either singly or in mixtures. As templates there may be mentioned, for example, tetraethyl ammonium compounds, cyclopentylamine, aminomethyl cyclohexane, piperidine, triethylamine, cyclohexylamine, trimethyl hydroxyethylamine, morpholine, dipropylamine (DPA), pyridine, isopropylamine and mixtures thereof. Preferred templates include tetraethyl ammonium hydroxide and salts, e.g., phosphate, fluoride, chloride, bromide and acetate, dipropylamine (DPA), triethylamine, cyclohexylamine, 1-methylamidazole, morpholine, pyridine, piperidine, and diethylethanolamine (DEA). The molecular sieve structure may be effectively controlled using combinations of templates.

In order to obtain molecular sieves with the desired high metal content, certain ratios of ingredients must be respected in the molecular sieve synthesis mixture. For example, a synthesis mixture for producing SAPO-34 according to the invention advantageously has a molar composition, within the following ranges:

| Components | Range | Preferred range |
|---|---|---|
| $P_2O_5:Al_2O_3$ | 0.6:1 to 1.2:1 | about 1:1 |
| $SiO_2:Al_2O_3$ | 0.01:1 to 0.5:1 | 0.1:1 to 0.5:1 |
| $H_2O:Al_2O_3$ | 10:1 to 100:1 | 15:1 to 60:1 | together with an organic template, advantageously tetraethylammonium hydroxide (TEAOH), dipropylamine (DPA), isopropylamine or morpholine, or a mixture of two or more such templates, in a proportion appropriate to yield SAPO-34.

In addition to the synthesis mixture components mentioned above, the synthesis mixture may also contain other components, e.g. water-miscible organic solvents. As water-miscible organic solvent there may be mentioned sulphoxides and $C_1$ to $C_5$ oxygenated hydrocarbons, the latter advantageously being an acid, aldehyde, ketone or mono- or polyhydric alcohol. As examples there may be mentioned ethylene glycol, 1,2- and 1,3-propanediols, acetone, methanol, n- and isopropanol, butanol and, preferably, ethanol. Preferably, the synthesis mixture is surfactant-free.

In general, the treatment of the synthesis mixture to yield the desired crystalline molecular sieve, usually termed hydrothermal treatment, is advantageously carried out under autogenous pressure, for example in an autoclave, for example a stainless steel autoclave which may, if desired, be ptfe-lined. The treatment may, for example, be carried out at a temperature within the range of from 50° C. to 250° C., advantageously from 90° C. to 250° C., especially 120° C. to 250° C., depending on the molecular sieve being made. The treatment may, for example, be carried out for a period within the range of from 1 to 200 hours, preferably up to 100 hours, again depending on the molecular sieve being formed. The procedure may include an ageing period, either at room temperature or, preferably, at a moderately elevated temperature, before the hydrothermal treatment at more elevated temperature. The latter may include a period of gradual or stepwise variation in temperature.

The treatment may be carried out with the vessel static or, preferably, with stirring or with rotating the vessel about a horizontal axis (tumbling). If desired, the synthesis mixture may be stirred or tumbled during an initial part of the heating stage, for example, from room temperature to an elevated, e.g., the final treatment, temperature, and be static for the remainder. Agitation generally produces a product with a smaller particle size and a narrower particle size distribution than static hydrothermal treatment.

The molecular sieves of the invention are useful as catalysts in various chemical processes, in particular in methanol to olefins conversion processes. For this purpose, the molecular sieves are usually calcined and/or formed into molecular sieve catalyst compositions before catalytic use.

The molecular sieves of the present invention may be combined with one or more formulating agents, to form a molecular sieve catalyst composition or a formulated molecular sieve catalyst composition. The formulating agents may be one or more materials selected from the group consisting of binding agents, matrix or filler materials and mixtures thereof. The formulated molecular sieve catalyst composition is formed into useful shape and sized particles by well-known techniques such as spray drying, pelletizing, extrusion, and the like.

Non-limiting examples of binders that are useful alone or in combination include various types of hydrated alumina, silicas, and/or other inorganic oxide sol. One preferred alumina containing sol is aluminium chlorhydrol. Upon heating, the inorganic oxide sol acts like glue binding the synthesized molecular sieves and other materials together. For example, an alumina sol will convert to aluminium oxide following heat treatment.

Aluminium chlorhydrol, a hydroxylated aluminium based sol containing a chloride counter ion, has the general formula of $Al_m O_n(OH)_o Cl_p \cdot x(H_2O)$ wherein m is 1 to 20, n is 1 to 8, o is 5 to 40, p is 2 to 15, and x is 0 to 30. In one embodiment, the binder is $Al_{13}O_4(OH)_{24}Cl_7 \cdot 12(H_2O)$ as is described in G. M. Wolterman, et al., Stud. Surf. Sci. and Catal., 76, pages 105–144 (1993), which is herein incorporated by reference.

The molecular sieve of the present invention may be combined with one or more matrix material(s). Non-limiting examples of matrix materials include one or more of the following: rare earth metals, metal oxides including titania, zirconia, magnesia, thoria, beryllia, quartz, silica or sols, and mixtures thereof, for example silica-magnesia, silica-zirconia, silica-titania, silica-alumina and silica-alumina-thoria. In one embodiment, matrix materials are natural clays such as those from the families of montmorillonite and kaolin. These natural clays include sabbentonites and those kaolins known as, for example, Dixie, McNamee, Georgia and Florida clays. Non-limiting examples of other matrix materials include: haloysite, kaolinite, dickite, nacrite, or anauxite. In one embodiment, the matrix material, preferably any of the clays, are subjected to well known modification processes such as calcination and/or acid treatment and/or chemical treatment.

In one preferred embodiment, the matrix material is a clay or a clay-type composition, preferably the clay or clay-type composition having a low iron or titania content, and most preferably the matrix material is kaolin. Kaolin has been found to form a pumpable, high solid content slurry; it has a low fresh surface area, and it packs together easily due to its platelet structure. A preferred average particle size of the matrix material, most preferably kaolin, is from about 0.1 $\mu$m to about 0.6 $\mu$m with a D90 particle size distribution of less than about 1 $\mu$m.

In one embodiment, the binder, the molecular sieve and the matrix material are combined in the presence of a liquid to form a molecular sieve catalyst composition. Upon combining the molecular sieve and the matrix material, optionally with a binder, in a liquid to form a slurry, mixing, preferably rigorous mixing is needed to produce a substantially homogeneous mixture containing the molecular sieve. Non-limiting examples of suitable liquids include one or a combination of water, alcohol, ketones, aldehydes, and/or esters. The most preferred liquid is water. In one embodiment, the slurry is colloid-milled for a period of time sufficient to produce the desired slurry texture, sub-particle size, and/or sub-particle size distribution.

The molecular sieve and matrix material, and the optional binder, may be in the same or different liquid, and may be combined in any order, together, simultaneously, sequentially, or a combination thereof. In the preferred embodiment, the same liquid, preferably water is used. The molecular sieve, matrix material, and optional binder, are combined in a liquid as solids, substantially dry or in a dried form, or as slurries, together or separately. If solids are added together as dry or substantially dried solids, it is preferable to add a limited and/or controlled amount of liquid.

The slurry of the molecular sieve, binder and matrix materials is mixed or milled to achieve a sufficiently uniform slurry of sub-particles of the molecular sieve catalyst composition that is then fed to a forming unit that produces the molecular sieve catalyst composition. In a preferred embodiment, the forming unit is spray dryer. Typically, the forming unit is maintained at a temperature sufficient to remove most of the liquid from the slurry, and from the resulting molecular sieve catalyst composition. The resulting catalyst composition when formed in this way takes the form of microspheres.

When a spray drier is used as the forming unit, typically, the slurry of the molecular sieve and matrix material, and optionally a binder, is co-fed to the spray drying volume with a drying gas with an average inlet temperature ranging from 200° C. to 550° C., and a combined outlet temperature ranging from 100° C. to about 225° C. The formulated molecular sieve catalyst composition contains from about 1% to about 99%, more preferably from about 5% to about 90%, and most preferably from about 10% to about 80%, by weight of the molecular sieve based on the total weight of the molecular sieve catalyst composition.

Once the molecular sieve catalyst composition is formed in a substantially dry or dried state, to further harden and/or activate the formed catalyst composition, a heat treatment such as calcination, at an elevated temperature is usually performed. A conventional calcination environment is air that typically includes a small amount of water vapour. Typical calcination temperatures are in the range from about 400° C. to about 1,000° C., preferably from about 500° C. to about 800° C., and most preferably from about 550° C. to about 700° C., preferably in a calcination environment such as air, nitrogen, helium, flue gas (combustion product lean in oxygen), or any combination thereof.

In a preferred embodiment, the molecular sieve catalyst composition is heated in nitrogen at a temperature of from about 600° C. to about 700° C. Heating is carried out for a period of time typically from 30 minutes to 15 hours, preferably from 1 hour to about 10 hours, more preferably from about 1 hour to about 5 hours, and most preferably from about 2 hours to about 4 hours.

In addition to the molecular sieve of the present invention, the catalyst compositions of the present invention may comprise one or several other catalytically active materials.

In another embodiment, the molecular sieve of the present invention may be bound to another molecular sieve, as disclosed for example in U.S. Pat. No. 5,972,203, PCT WO 98/57743, U.S. Pat. No. 6,300,535, and mesoporous molecular sieves. Binder may no longer be necessary in such systems. In a further embodiment, the molecular sieve of the present invention may be combined with a metal catalyst, for example as a Fischer-Tropsch catalyst.

Catalyst compositions comprising the molecular sieves of the invention are useful in various chemical processes. The preferred processes of the present invention include processes directed to the conversion of a feedstock comprising one or more oxygenates into one or more olefin(s) and processes directed to the conversion of a feedstock comprising one or more oxygenates and ammonia into alkyl amines, in particular methylamines.

In a preferred embodiment of the processes of the invention, the feedstock contains one or more oxygenates, more specifically, one or more organic compound(s) containing at least one oxygen atom. In the most preferred embodiment of the process of the invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts.

Non-limiting examples of oxygenates include methanol, ethanol, n-propanol, isopropanol, methyl ethyl ether, dimethyl ether, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, dimethyl ether, diethyl ether or a combination thereof, more preferably methanol and dimethyl ether, and most preferably methanol.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as methanol-to-olefins (MTO). In a MTO process, an oxygenated feedstock, most preferably a methanol containing feedstock, is converted in the presence of a molecular sieve catalyst composition into one or more olefin(s), preferably and predominantly, ethylene and/or propylene, often referred to as light olefin(s).

In addition to the oxygenate(s), the feedstock can contain one or more diluent(s), typically used to reduce the concentration of the oxygenate in the feedstock. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred.

In one embodiment, the amount of diluent in the feedstock is in the range of from about 1 to about 99 mole percent, preferably from about 1 to 80 mole percent, more preferably from about 5 to about 50 mole percent, most preferably from about 5 to about 25 mole percent, based on the total number of moles of the feedstock and diluent.

The process for converting a feedstock containing one or more oxygenates, in the presence of a molecular sieve catalyst composition of the invention, is carried out in a reactor, operated as a fixed or fluidized (including turbulent) bed reactor. Preferably, the process is a continuous fluidised bed process, and most preferably a continuous high velocity fluidised bed process. Suitable conventional reactor types are described in for example U.S. Pat. Nos. 4,076,796, 6,287,522, and Fluidization Engineering, D. Kunii and O. Levenspiel, Robert E. Krieger Publishing Company, New York, N.Y. 1977, which are all herein fully incorporated by reference.

The preferred reactors are riser reactors generally described in Riser Reactor, Fluidization and Fluid-Particle Systems, pages 48 to 59, F. A. Zenz and D. F. Othmo, Reinhold Publishing Corporation, New York, 1960, U.S. Pat. No. 6,166,282, and U.S. patent application Ser. No. 09/564,613 filed May 4, 2000, which are all herein fully incorporated by reference.

In the preferred embodiment, a fluidised bed process or high velocity fluidised bed process includes a reactor system, a regeneration system and a recovery system.

The reactor system preferably is a fluid bed reactor system having a first reaction zone within one or more riser reactor(s) and a second reaction zone within at least one disengaging vessel, preferably comprising one or more cyclones. In one embodiment, the one or more riser reactor(s) and disengaging vessel is contained within a single reactor vessel. Fresh feedstock, preferably containing one or more oxygenates, optionally with one or more diluent(s), is fed to the one or more riser reactor(s) in which a molecular sieve catalyst composition and/or coked version thereof is introduced. In one embodiment, the molecular sieve catalyst composition and/or coked version thereof is contacted with a liquid or gas, or combination thereof, prior to being introduced to the riser reactor(s). Preferably the liquid is water or methanol, and the gas is an inert gas such as nitrogen.

In an embodiment, the amount of fresh feedstock fed separately or jointly with a vapour feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapour feedstocks are preferably the same composition, or contain varying proportions of the same or different feedstock with the same or different diluent.

The feedstock entering the reactor system is preferably converted, partially or fully, in the first reactor zone into a gaseous effluent that enters the disengaging vessel along with a coked molecular sieve catalyst composition. In the preferred embodiment, cyclone(s) within the disengaging vessel are designed to separate the molecular sieve catalyst composition, preferably a coked molecular sieve catalyst composition, from the gaseous effluent containing one or more olefin(s) within the disengaging zone. Gravity effects within the disengaging vessel will also separate the catalyst compositions from the gaseous effluent. Other methods for separating the catalyst compositions from the gaseous effluent include the use of plates, caps, elbows, and the like.

In one embodiment of the disengaging system, the disengaging system includes a disengaging vessel; typically a lower portion of the disengaging vessel is a stripping zone. In the stripping zone the coked molecular sieve catalyst composition is contacted with a gas, preferably one or a combination of steam, methane, carbon dioxide, carbon monoxide, hydrogen, or an inert gas such as argon, preferably steam, to recover adsorbed hydrocarbons from the coked molecular sieve catalyst composition that is then introduced to the regeneration system. In another embodiment, the stripping zone is in a separate vessel from the disengaging vessel and the gas is passed at a gas hourly superficial velocity (GHSV) of from 1 $hr^{-1}$ to about 20,000 $hr^{-1}$ based on the volume of gas to volume of coked molecular sieve catalyst composition, preferably at an elevated temperature from 250° C. to about 750° C., preferably from about 350° C. to 650° C., over the coked molecular sieve catalyst composition.

The conversion temperature employed in the conversion process, specifically within the reactor system, is in the range of from about 200° C. to about 1000° C., preferably from about 250° C. to about 800° C., more preferably from about 250° C. to about 750° C., yet more preferably from about 300° C. to about 650° C., yet even more preferably from about 350° C. to about 600° C., most preferably from about 350° C. to about 550° C.

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV) is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidised state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$; preferably the WHSV for conversion of a feedstock containing methanol and dimethyl ether is in the range of from about 20 $hr^{-1}$ to about 300 $hr^{-1}$.

The superficial gas velocity (SGV) of the feedstock including diluent and reaction products within the reactor system is preferably sufficient to fluidise the molecular sieve catalyst composition within a reaction zone in the reactor. The SGV in the process, particularly within the reactor system, more particularly within the riser reactor(s), is at least 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

In one preferred embodiment of the process for converting an oxygenate to olefin(s) using a SAPO molecular sieve, the process is operated at a WHSV of at least 20 $hr^{-1}$ and a Temperature Corrected Normalized Methane Selectivity (TCNMS) of less than 0.016, preferably less than or equal to 0.01. See for example U.S. Pat. No. 5,952,538 016, which is herein fully incorporated by reference.

In another embodiment of the processes for converting an oxygenate such as methanol to one or more olefin(s) using a SAPO molecular sieve, the WHSV is from 0.01 $hr^{-1}$ to about 100 $hr^{-1}$, at a temperature of from about 350° C. to 550° C. See for example EP-0 642 485 B1, which is herein fully incorporated by reference.

Other processes for converting an oxygenate such as methanol to one or more olefin(s) using a molecular sieve catalyst composition are described in PCT WO 01/23500 published Apr. 5, 2001, which is herein incorporated by reference. In this document, selectivity to propane is reduced by adjusting the MTO process parameters. The present invention provides an MTO process in which selectivity to propane is further reduced, due to the specific properties of the molecular sieve catalyst.

After a certain time of catalyst use, the molecular sieves used for converting oxygenates lose catalytic activity due to the deposit of reaction by-products, referred to as coke, on the catalyst. Catalytic activity can be restored by removing these coke deposits, i.e. regenerating the catalyst. However it is desirable to have catalysts with the longest possible catalyst life before requiring regeneration. According to the present invention, metalloaluminophosphate molecular sieves having high metal content and small particle sizes have longer catalyst lifes than other molecular sieves.

Once the molecular sieve has lost its catalytic activity due to coking, the coked molecular sieve is withdrawn from the disengaging vessel, preferably by one or more cyclones(s), and introduced to the regeneration system. The regeneration system comprises a regenerator where the coked catalyst composition is contacted with a regeneration medium, preferably a gas containing oxygen, under general regeneration conditions of temperature, pressure and residence time.

Non-limiting examples of the regeneration medium include one or more of oxygen, $O_3$, $SO_3$, $N_2O$, NO, $NO_2$, $N_2O_5$, air, air diluted with nitrogen or carbon dioxide, oxygen and water (U.S. Pat. No. 6,245,703), carbon monoxide and/or hydrogen. The regeneration conditions are those capable of burning coke from the coked catalyst composition, preferably to a level less than 0.5 weight percent based on the total weight of the coked molecular sieve catalyst composition entering the regeneration system. The coked molecular sieve catalyst composition withdrawn from the regenerator forms a regenerated molecular sieve catalyst composition.

The regeneration temperature is in the range of from about 200° C. to about 1500° C., preferably from about 300° C. to about 1000° C., more preferably from about 450° C. to about 750° C., and most preferably from about 550° C. to 700° C. The regeneration pressure is in the range of from about 15 psia (103 kPaa) to about 500 psia (3448 kPaa), preferably from about 20 psia (138 kPaa) to about 250 psia (1724 kPaa), more preferably from about 25 psia (172 kPaa) to about 150 psia (1034 kPaa), and most preferably from about 30 psia (207 kPaa) to about 60 psia (414 kPaa).

The burning of coke is an exothermic reaction, and in an embodiment, the temperature within the regeneration system is controlled by various techniques in the art including feeding a cooled gas to the regenerator vessel, operated either in a batch, continuous, or semi-continuous mode, or a combination thereof. A preferred technique involves withdrawing the regenerated molecular sieve catalyst composition from the regeneration system and passing the regenerated molecular sieve catalyst composition through a catalyst cooler that forms a cooled regenerated molecular sieve catalyst composition. The catalyst cooler, in an embodiment, is a heat exchanger that is located either internal or external to the regeneration system.

The gaseous effluent containing the light olefin products is withdrawn from the disengaging system and is passed through a recovery system. There are many well-known recovery systems, techniques and sequences that are useful in separating olefin(s) and purifying olefin(s) from the gaseous effluent. Recovery systems generally comprise one or more or a combination of a various separation, fractionation and/or distillation towers, columns, splitters, or trains, reaction systems such as ethylbenzene manufacture (U.S. Pat. No. 5,476,978) and other derivative processes such as aldehydes, ketones and ester manufacture (U.S. Pat. No. 5,675,041), and other associated equipment for example various condensers, heat exchangers, refrigeration systems or chill trains, compressors, knock-out drums or pots, pumps, and the like.

The molecular sieves of the present invention may also be used in the manufacture of alkylamines, using a feedstock comprising ammonia in addition to oxygenates. Examples of suitable processes are as described in published European Patent Application EP 0 993 867 A1, and in U.S. Pat. No. 6,153,798 to Hidaka et. al, which are herein fully incorporated by reference.

EXAMPLES

The following Examples, in which parts are by weight unless otherwise indicated, illustrate specific embodiments within the overall scope of the invention as claimed. The source and purity of starting materials are those first given, unless indicated otherwise.

In these examples, crystal morphology and sizes were determined by visual analysis of electron microscopy pictures taken on a Hitachi S-4500 scanning electron microscope using an accelerating voltage of 1.2 to 1.4 kV. X-ray diffraction patterns were obtained on a Siemens D500 diffractometer using Cu radiation, 1° divergence and antiscatter slits, secondary graphite monochromator, and scintillation counter. Patterns were collected in step scan mode from 2.00 to 50.00° 2θ with a step scan size of 0.02° 2θ and a counting time of 1 sec.

Example 1

This example illustrates the manufacture of SAPO-34 according to the invention, having a cubic-like crystal morphology with edges of less than 0.1 microns and a Si/Al atomic ratio of 0.189.

A synthesis mixture was prepared as follows: 19.7 parts of $H_3PO_4$ (85%, available from Aldrich), 47.2 parts of ethanol, 5.3 parts of tetraethylortho-silicate (TEOS, available from Petrarch), 11.8 parts of alumina hydrate (Catapal B, Condea Vista, 74% $Al_2O_3$, 26% $H_2O$, available from Sasol Chemical Industries), 71.8 parts of tetraethylammonium hydroxide (TEAOH, 35% in water, available from SACHEM, Inc.) and 4.20 parts of deionized water were mixed together, to yield a synthesis mixture of molar composition:

$$Al_2O_3:P_2O_5:0.3SiO_2:2TEAOH:40H_2O:12C_2H_5OH$$

The synthesis mixture was placed in a ptfe-lined stainless steel autoclave, which was mounted on a shelf in an air oven, the shelf being rotated, tumbling the autoclave at 12 rpm, and maintained at 200° C. for 24.5 hours. After cooling, the product was recovered by centrifuging, washed with water, and dried in an air oven. The powder X-ray diffraction (XRD) pattern showed the product to be SAPO-34. The relatively broad diffraction peaks indicated a small crystal size. Elemental analysis: Si, 3.4%; Al, 17.4%; P, 16.4%, representing a product stoichiometry of $Si_{0.093} Al_{0.498} P_{0.409}$ (Si/Al=0.189).

SEM analysis showed that the crystals had cubic-like morphology with crystal dimensions less than 0.1 μm (crystal edges between 0.05 and 0.1 μm).

Example 2

This example illustrates the manufacture of SAPO-34 having a cubic-like crystal morphology with edges between 0.1 and 0.4 microns and a Si/Al atomic ratio of 0.179.

Using the procedure of example 1, a synthesis mixture of the following molar composition was prepared:

$$Al_2O_3:P_2O_5:0.3SiO_2:1.52TEAOH:30H_2O:16C_2H_5OH$$

The synthesis mixture was placed in a ptfe-lined stainless steel autoclave, which was mounted on a shelf in an air oven, the shelf being rotated, tumbling the autoclave at 12 rpm, and maintained at 200° C. for 24.5 hours. After cooling, the product was recovered by centrifuging, washed with water, and dried in an air oven. The powder X-ray diffraction (XRD) pattern showed the product to be SAPO-34.

Elemental analysis: Si, 3.24%; Al, 17.35%; P, 16.74%, representing a product stoichiometry of $Si_{0.089} Al_{0.495} P_{0.416}$ (Si/Al=0.179).

SEM analysis showed that the crystals had cubic-like morphology with crystal dimensions greater than 0.1 μm (crystal edges between 0.1 and 0.4 μm).

Example 3

This example illustrates the manufacture of SAPO-34 having a square platelet-like crystal morphology with edges between 0.25 and 1.0 microns, a thickness between 0.05 and 0.2 microns and a Si/Al atomic ratio of 0.175.

A synthesis mixture was prepared from the following components in the proportions (by weight) shown.

| Component | | Proportion |
|---|---|---|
| A | $H_3PO_4$ (Aldrich), 85% in water | 23.2 |
| | Water | 20.0 |
| | $Al_2O_3$ (Catapal A, Condea Vista) | 13.9 |
| B | TEAOH, (SACHEM) 35% in water | 84.5 |
| | Colloidal silica (Ludox HS-40, DuPont) 40% in water | 4.5 |
| | Total | 150.0 |

Phosphoric acid, water and alumina were mixed for 2 minutes and aged for 5 minutes at ambient temperature, the resulting mixture forming Component A. TEAOH, the silica and water were mixed for 2 minutes, the resulting mixture forming Component B.

Components A and B were combined and transferred to a stainless steel blender. The mixture was thoroughly homogenized in the blender for 5 minutes. The molar composition of the mixture was:

$$Al_2O_3:P_2O_5:0.3SiO_2:2.0TEAOH:52H_2O$$

The synthesis mixture was heated in a ptfe lined stainless steel autoclave to 175° C. and maintained at that temperature under static conditions for 88.5 hours. After cooling, the solid product was recovered by centrifugation, washed four times with water and dried overnight at 115° C. in an air oven.

The powder X-ray diffraction (XRD) pattern showed the product to be SAPO-34. Elemental analysis: Si, 3.13%; Al, 17.2%; P, 16.6%, representing a product stoichiometry of $SiO_{0.087} Al_{0.496} P_{0.417}$ (Si/Al=0.175). SEM analysis showed that the crystals had square platelet-like crystal morphology with edges between 0.25 and 1.0 microns and a thickness between 0.05 and 0.2 microns.

Example 4

This example illustrates the manufacture of SAPO-34 having a cubic-like crystal morphology with edges between 10 and 30 microns and a Si/Al atomic ratio of 0.20.

A synthesis mixture was prepared from the following components in the proportions (by weight) shown.

| Component | | Proportion |
|---|---|---|
| A | $H_3PO_4$ (Aldrich) 85% in water | 12.2 |
| | Water | 20.0 |
| | $Al_2O_3$ (Catapal A, Condea Vista) | 7.28 |
| B | DPA (dipropylamine, Aldrich) | 13.4 |
| C | Colloidal silica (Ludox HS-40, duPont) 40% in water | 3.17 |
| | Water | 19.0 |
| | SAPO-34 seeds (prepared as in example 1) | 0.050 |
| | Total | 75.0 |

Phosphoric acid, water and alumina were mixed for 2 minutes, aged for 5 minutes at ambient temperature, and mixed again for 1 minute, the resulting mixture forming Component A. DPA was added to Component A, the resulting mixture forming Component B which was mixed for 1 minute. The colloidal silica and water, forming Component C were added to Component B. The resulting reaction mixture was transferred to a stainless steel blender and was thoroughly homogenized in the blender for 5 minutes. The molar composition of the mixture was:

$$Al_2O_3:P_2O_5:0.4SiO_2:2.5DPA:50H_2O$$

The synthesis mixture was heated in a ptfe lined stainless steel autoclave to 200° C. and maintained at that temperature while the autoclave was rotated at 10 rpm for 45.5 hours. After cooling, the solid product was recovered by filtration, washed four times with water and dried overnight at 115° C. in an air oven.

The powder X-ray diffraction (XRD) pattern showed the product to be SAPO-34. Elemental analysis: Si, 3.77%; Al, 18.1%; P, 16.2%, representing a product stoichiometry of $Si_{0.101}Al_{0.505}P_{0.394}$ (Si/Al =0.20). SEM analysis showed that the crystals had cubic-like morphology with crystal edges between 10 and 30 μm.

Example 5

This example illustrates the manufacture of crystals of a mixed phase of CHA/AEI having a morphology of half-cubes with longest edges between 0.3 to 0.6 microns and a Si/Al atomic ratio of 0.07.

A solution of 33.66 gr of phosphoric acid (85% in water), 32.88 gr of de-mineralized water, and 61.6 gr of a TEAOH solution (35% in water) was prepared in a glass beaker. To this solution were added 2.23 gr of Ludox AS 40 (40% silica). 19.9 gr of alumina (Condea Pural SB) were added and a slurry was obtained with the following composition expressed as molar ratios:

$$0.1SiO_2:P_2O_5:Al_2O_3:TEAOH:35H_2O$$

This slurry was mixed until homogeneous and transferred to a 150 ml stainless steel autoclave. This autoclave was mounted on a rotating axis in an oven. The axis was rotated at 60 rpm and the oven was heated in 8 hours to 175° C. The autoclave was kept at this temperature for 48 hours. After cooling to room temperature, a sample was taken and washed and dried.

Example 6

This example illustrates the catalytic performance of the crystalline molecular sieves prepared at Examples 1, 2, 3 and 5 in the conversion of an oxygenate feedstock into light olefins.

The molecular sieves, hereinafter referred to as catalysts, were tested as follows. Before testing, each catalyst was calcined in a muffle oven at 600° C. in air for one hour to remove the template. Catalyst was loaded into a fixed bed reactor. A methanol feedstock was prepared by sparging argon through a vessel containing methanol at a fixed temperature. The resulting feedstock contained 70 to 100 torr of methanol in argon. The total pressure was 760 torr. The argon/methanol feedstock was passed across the catalyst bed at 450° C. and a WHSV (Weight Hourly Space Velocity) of 300–1000. The reactor effluent was passed to both an on-line mass spectrometer and an on-line gas chromatograph.

The activity of each catalyst is provided in Table 1. The activity is determined by taking the measured conversion value and inserting it into the following equation (first order rate equation):

$$A=\ln(1-C_{MeOH})*(F_{MeOH}/60*0.7912/32)/I_{MeOH}/(W_{MS}/1500)$$

wherein $C_{MeOH}$ is the methanol conversion in percent;
A is the activity expressed in k(1/sec);
$F_{MeOH}$ is the methanol feed rate expressed in ml/minute;
$I_{MeOH}$ is the initial methanol concentration expressed in moles/liter;
$W_{MS}$ is the weight of molecular sieve expressed in grams.

TABLE 1

| | Catalyst of Example | | | |
|---|---|---|---|---|
| | 1 | 2 | 3 | 5 |
| Crystal dimensions (μm) | 0.05–0.1 | 0.1–0.4 | 0.25–1.0 | 0.3–0.6 |
| Si/Al | 0.189 | 0.179 | 0.175 | 0.07 |
| Activity k (1/sec) | 580 | 480 | 310 | 150 |

Figure 2:
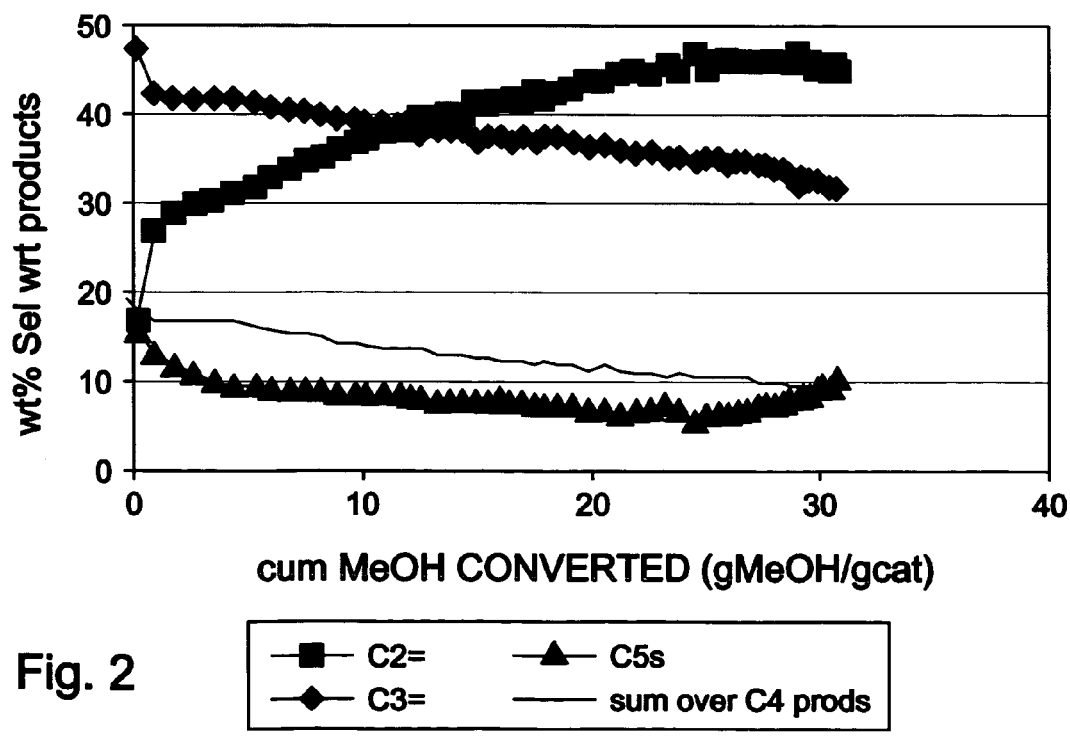
FIG. 2 shows the selectivities for ethylene (C2=), propylene (C3=), hydrocarbon products having 4 carbon atoms and hydrocarbon products having 5 carbon atoms for a SAPO-34 having crystal dimensions of less than 0.1 micron and a Si/Al atomic ratio of 0.189.

The selectivities for ethylene (C2=), propylene (C3=), hydrocarbon products having 4 carbon atoms and hydrocarbon products having 5 carbon atoms is shown in FIG. 1 for the catalyst prepared at example 3 and in FIG. 2 for the catalyst prepared at Example 1.

Example 7

The catalysts prepared at Examples 1 to 5 were tested at 500° C. and 25 psig in a plug flow reactor equipped with on-line gas chromatography analysis. The catalyst selectivity data are provided in Table 2, in which E refers to the ethylene selectivity, P refers to the propylene selectivity and Propane refers to the propane selectivity.

TABLE 2

| | Catalyst of Example | | | | |
|---|---|---|---|---|---|
| | 1 | 2 | 3 | 4 | 5 |
| Crystal dimensions (μm) | 0.05–0.1 | 0.1–0.4 | 0.25–1.0 | 10–30 | 0.3–0.6 |
| Si/Al | 0.189 | 0.179 | 0.175 | 0.20 | 0.07 |
| WHSV | 500 | 500 | 500 | 500 | 300 |
| E + P (%) | 75.8 | 76.0 | 75.2 | 68.8 | 77.0 |
| E/P | 0.80 | 0.87 | 0.85 | 0.83 | 0.79 |
| Propane (%) | 0.5 | 0.6 | 0.7 | 2.0 | 0.4 |

The results from Table 2 show that small crystals with high Si/Al ratios have comparable catalytic performance to the catalyst of example 5 with a low Si/Al ratio.

This demonstrates that the molecular sieve can be tailored to enable significantly higher activity while maintaining selectivity to light olefins. The higher activity (or Si content) allows to use less sieve while achieving the same conversion. Also, the high activity sieve according to the present invention has low selectivity to undesired products such as propane, comparable to the propane selectivity of the low activity catalyst of example 5.

The invention claimed is:

1. A process for converting an oxygenate feedstock to light olefins which comprises contacting the oxygenate feedstock under catalytic conversion conditions with a catalyst, the catalyst comprising a crystalline metalloaluminophosphate molecular sieve having a chemical composition on an anhydrous basis expressed by an empirical formula of $$(EL_xAl_yP_z)O_2$$

where EL is a metal selected from the group consisting of silicon, germanium and mixtures thereof, "x" is the mole fraction of EL and has a value of greater than 0.05, "y" is the mole fraction of Al and has a value of at least 0.01, "z" is the mole fraction of P and has a value of at least 0.01 and x+y+z=1 and wherein x/y is greater than 0.15, the molecular sieve crystals having at least one crystal dimension of less than 0.2 micron.

2. The process of claim 1, wherein the molecular sieve crystals have all crystal dimensions of less than 0.2 micron.

3. The process of claim 1, wherein the molecular sieve crystals have at least one crystal dimension of less than 0.15 micron.

4. The process of claim 1, wherein the molecular sieve crystals have at least one crystal dimension of less than 0.1 micron.

5. The process of claim 3, wherein x has a value of at least 0.07.

6. The process of claim 5, wherein x has a value of at least 0.08.

7. The process of claim 6, wherein x has a value of at least 0.09.

8. The process of claim 1, wherein El is silicon.

9. The process of claim 1, wherein x/y is at least 0.17.

10. The process of claim 9, wherein x/y is at least 0.18.

11. The process of claim 8, wherein the molecular sieve is selected from the group consisting of SAPO-5, SAPO-11, SAPO-18, SAPO-34, SAPO-35, SAPO-41, SAPO-56, mixtures thereof and intergrown forms thereof.

12. The process of claim 11, wherein the molecular sieve is SAPO-34.

13. The process of claim 1, wherein the oxygenate is selected from methanol, dimethyl ether and mixtures thereof.

* * * * *